United States Patent [19]

Fymat et al.

[11] Patent Number: 4,682,604

[45] Date of Patent: Jul. 28, 1987

[54] COINCIDENCE COUNTING EMISSION TOMOGRAPHIC PROBE: METHOD AND APPARATUS

[75] Inventors: Alain L. Fymat, Pasadena; Wai-Nang P. Lee, Van Nuys; Moses A. Greenfield, Sherman Oaks, all of Calif.

[73] Assignee: The Regents of the University of California, Berkeley, Calif.

[21] Appl. No.: 705,916

[22] Filed: Feb. 25, 1985

[51] Int. Cl.[4] ............................................. A61B 6/00
[52] U.S. Cl. .................................. 128/659; 250/363 S
[58] Field of Search ................................. 128/653–654, 128/659; 250/363 S, 5 A, 5 B, 367–368

[56] References Cited

U.S. PATENT DOCUMENTS

| | | | |
|---|---|---|---|
| 4,243,652 | 1/1981 | Francis | 128/659 X |
| 4,247,774 | 1/1981 | Brooks | 250/367 |
| 4,395,635 | 7/1983 | Friauf et al. | 250/363 SA |
| 4,511,799 | 4/1985 | Bjorkholm | 250/367 |

FOREIGN PATENT DOCUMENTS 512672  3/1976  U.S.S.R. ................. 128/659

Primary Examiner—Kyle L. Howell
Assistant Examiner—Francis Jaworski
Attorney, Agent, or Firm—Poms, Smith, Lande & Rose

[57] ABSTRACT

This invention comprises a method and apparatus for measuring both the absolute levels and variations of radioactivity emitted following administration of suitable radioisotopes during a test period by selected organs. Miniaturized radiation detectors for measuring two different types of radiation, such as gamma rays and photons, for example, are modified by the addition of mutual overlap coincidence units, scalers, single channel analyzers and time-gates. The individual detector units are appropriately arranged to form a probe or collar in either a strip or a checkerboard configuration, extending around the neck to study the thyroid gland or other gland organ to be analyzed. The associated electronic architecture is appropriately designed in either simplex or multiplex circuit patterns. Measurements are performed according to an established, preprogrammed time schedule that is reflective of the functional processes of the organ undergoing testing, and which separately determine the background radiation and that emanating from the organ or gland being examined. The data is recorded and processed by a dedicated microcomputer means. With a properly chosen radiopharmaceutical, the measurements provide specific data useful for clinical evaluation of the physiological functions and morphological features of the organ.

17 Claims, 19 Drawing Figures

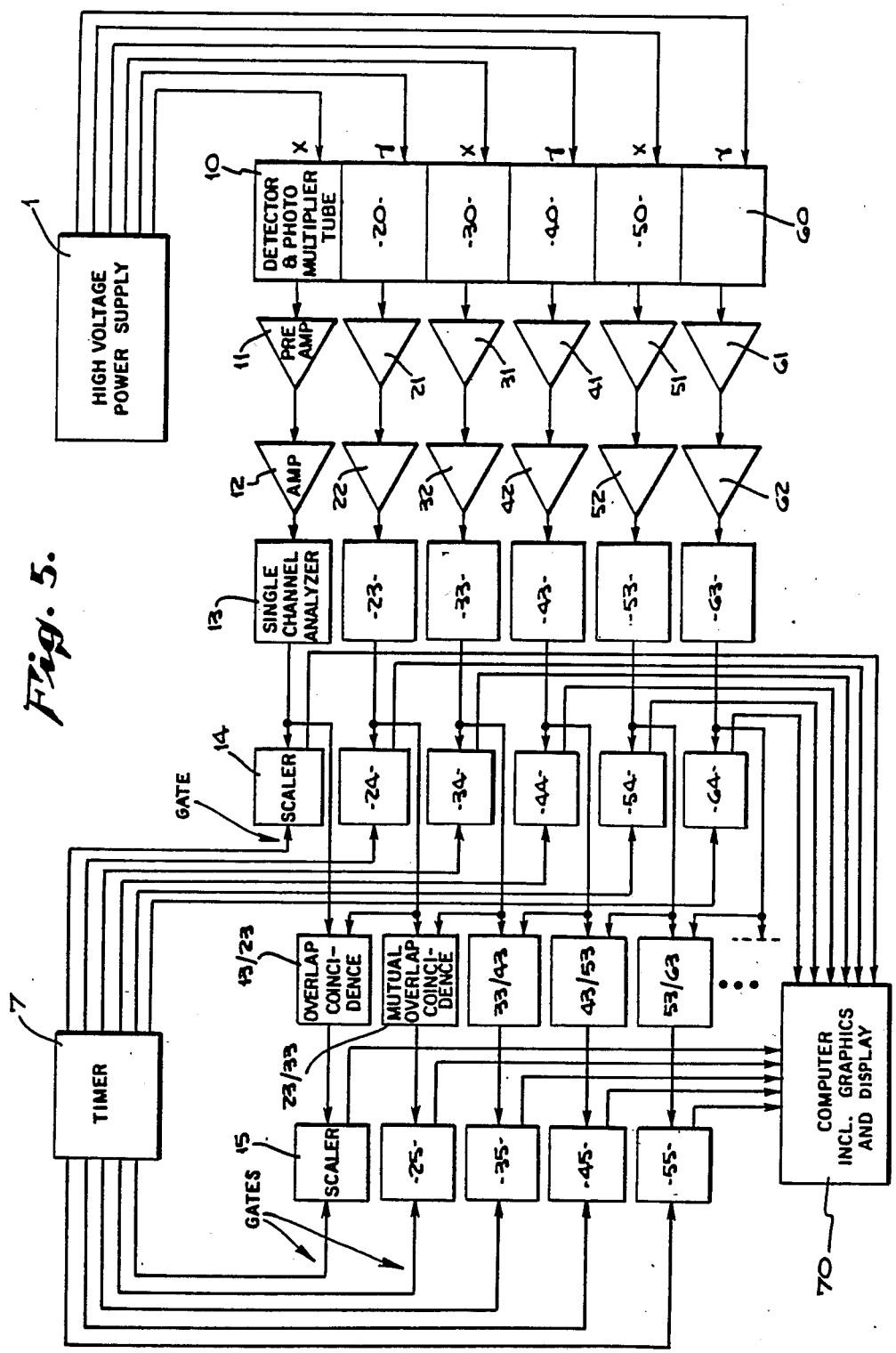

COINCIDENCE COUNTING EMISSION TOMOGRAPHIC PROBE: METHOD AND APPARATUS

The U.S. Government has a paid-up license in this invention and the right in limited circumstances to require the patent owner to license others on reasonable terms as provided for by the terms of Grant No. CA09092 awarded by the Department of Health and Human Services.

FIELD OF THE INVENTION

The present invention relates, in general, to methods and apparatus for monitoring and analyzing medically significant functions and features of a particular organ, and more particularly, provides a method and instrument to monitor and analyze emissions of radiations of different energies by an organ into which a radioactive drug (also known as a radiopharamaceutical) has been introduced, whereby both physiological and morphological determinations can be rendered.

BACKGROUND OF THE INVENTION

The present invention generally relates to a method and apparatus for performing in vivo analyses of the time-varying absolute radioactivity of selected human organs following intravenous injection or oral administration of a radiopharmaceutical. More particularly, the present invention concerns a nuclear medicine technique and instrument which may be employed to quantitate the absolute activities of a physiologically important radioactive isotope within an organ over a predetermined test period. The time activity relationship can be used to analyze physiological factors—that is, the functions and activity of an organ, including the physical and chemical processes involved—such as to give the regional blood flow to the organ and the metabolic function of the organ as represented by the radioactively labelled drug by the organ. The device also can function to determine the morphological factors—that is, the form and structure—of an organ, such as depth within the patient. This invention is applicable, for example, to the diagnosis of diseases of the thyroid and the kidneys and to the localization of tumors using labelled antibodies.

The prior art is best described with respect to the particular case of devices for diagnostic techniques used on the thyroid gland. The principal function of the thyroid is to regulate the body's general metabolism. For this purpose, it requires iodine (from salt in the diet). In the absence of iodine accumulation, this regulatory function cannot be performed. The assessment of this gland's morphology and physiology by nuclear medicine procedures is one of the oldest clinical procedures. It is practiced in most hospitals and other orgainizations providing medical care which are licensed to handle radioisotopes.

In contrast with the apparatus described herein, prior art instruments currently use imaging and scanning techniques. Tomographic imaging scanners are usually classified into two general categories: planar tomographs, where the image corresponds to the distribution of radioactivity in longitudinal planes parallel to the head-to-toe axis of the patient, and transverse tomographs, yielding an analogous image in cross-sectional planes perpendicular to all planes containing the head-to-toe axis direction. Thus, for example, well-known devices such as the positron camera of Brownell & Burnham and the multiplane scanner of Anger are plane tomographs. Kuhl & Edwards' scanner and the newer ECAT (Emission Computed Axial Tomography) and PET (Position Emission Tomography) axial scanners are transverse tomographs devices. The instrument of Brownell & Burnham, the ECAT and the PET utilize the properties of positron-emission radionuclides which yield gamma radiation from annihilation of the positron and the electron essentially to the site of the radionuclide. The radiation consists of highly energetic gamma photons (511 KeV) ejected 180 degrees apart, thus requiring opposing nuclear counters for their detection.

With the increased knowledge of the biologic effects of ionizing radiations, and the parallel increased applications of tracer techniques, there has taken place a growing concern regarding post-treatment effects of exposure to ionizing radiations and the possible parallel deleterious aftereffects of repeated exposure to low doses of radiation. However, there currently exists no clinically documented evidence or established association between the use of radiopharmaceuticals in the diagnoses of thyroid carcinoma. Nonetheless, the radiation exposure to the organ is cumulative in nature and the physicochemical and medical communities are endeavoring to reduce the radiation dose to the thyroid gland while at the same time preserving diagnostic information value of nuclear medicine techniques. The evolution of radiopharmaceutical developments in preparing short-lived radioisotopes, and biological material labelled with these isotopes, offers new alternatives to traditional approaches. However, when coupled with new concepts in nuclear instrumentation technology, further beneficial advantages could be gained in the areas of radiation dose reduction and enhanced diagnostic accuracy.

The continuing primary use of the iodine isotope I-131 represents comparatively one of the larger increments of radiation dose delivered by nuclear medicine applications. Its diagnostic value is also impaired by the inaccuracy of conventional measurement techniques because of background radiation from surrounding tissue and blood flow and the required correction for attenuation due to the presence of intervening tissue. Thus in current practice, critical corrections for extra-thyroidal neck activity and for radiation attenuation by the intervening tissues between the thyroid and the neck surface are required prior to determining the percent of radio-iodine uptake by the thyroid.

Accordingly, it is an object of the present invention to provide an analytical method and instrument arrangement that enables the organ depth in the body, the absolute radioactivity of this organ, and the radioactivity of the surrounding tissues, to be measured concurrently over the duration of the test.

It is another object of the present invention to provide an analytical method and instrument arrangement that enables the physiologic functions of uptake, retention and excretion of radioactive labelled substrates by the organ, and their relative equilibrium regime, to be assessed concurrently.

It is a further object of the present invention to provide an analytical method and apparatus for obtaining information about the fractional cardiac output to the organ.

Another object of the invention is to reduce the dosages of radiopharmaceuticals required in nuclear medicine techniques.

SUMMARY OF THE INVENTION

This invention is distinct from other radioactive emission tomographic systems in the clinical objective of the test, the physicochemical mechanisms involved, the instrument arrangement required, and the resultant data provided. The invention provides a method to investigate quantitatively the physiologic functions of blood flow, uptake, retention and excretion of selected human organs with a diagnostic precision that involves minimal doses of radiopharmaceuticals. It does not reconstruct an image of the organ by scanning or otherwise (although the concept can probably be extended to scanning modes). It involves the detection of multiple low-energy photons emitted in all directions during electron capture decay.

Briefly described, the present invention involves a technique and an apparatus that is useful in nuclear medicine as well as in multi-energy coincident photon emission tomography.

More particularly, the subject instrument includes a probe or a ring, or multiple rings, arranged to form a collar around the body part of interest, of miniaturized crystalline detectors. These detectors are distinguished by the two different photon energies they are intended to register, e.g. X-radiation photons and gamma-radiation photons.

In the single probe version of this instrument, a detector pair is abuttingly aligned, whereby the angle between the receiving surfaces can be varied in order to orient the probe with respect to the body part in which the organ to be monitored and analyzed is located. Each detector unit is augmented by a photomultiplier tube and sequentially connected to a preamplifier, an amplifier, a single channel analyzer and a scaler. In the collar-like embodiment, a plurality of paired detectors may be employed.

Every two successive paired units are connected to an overlap coincidence unit and a scaler, and every two successive pairs are likewise connected to a mutual overlap coincidence unit and a scaler. All scalers are time-gated following a pre-established schedule appropriate to the physiology of the organ under test. The registered overlap and mutual overlap coincidence emissions are processed and analyzed in a digital computer.

In the double-ring version of this instrument, the detector units can be arranged such that they form either a checkerboard or a strip pattern. The multiple-ring version is an extension of the double-ring version into a rectangular array.

The electronic architecture of the subject instrument can follow a simplex pattern, in which all possible pairings of two detector units corresponding to two different energies are electronically connected for coincidence. Alternatively, in order to enhance the number of coincidence events, as may be required for dose reduction or for low-uptake type patients, a multiplex pattern is employed in which every detector unit of a given energy is connected with all other detector units of the other energy.

Following energization from a stable high voltage power supply, the instrument records the energetically different emissions, and their coincident events of summed energies, at all locations around the patient's body or body part of interest. At any preset time, the counts recorded for either of the photon energies and for the coincident energy sum, follow a modulation curve in which the maximum and the minimum are attained at angular positions that are independent of the organ depth. Additionally, the counts for different depths are all equal at nodal positions located 90° on either side of the extremal positions. For the radioactivity counts derived from the above, the variations are similar except for the nodes which are now located at half the earlier angular distance from the extrema. The resulting data at the nodes and at the extrema, and their time variations, are then recorded and processed by a computer in the calculation of the organ absolute activity, the surrounding tissue background activity, the organ depth, the radiopharmaceutical uptake, retention, and equilibrium pattern of the organ, and the fractional cardiac output to the organ. Through determination of the background radiation levels, at the nodal points mentioned above, a much more accurate analysis of the thyroid absorption and retention of the radio pharmaceutical material may be accomplished.

Dose reduction, concurrent determination of the extra-thyroidal neck activity, location of the gland within the neck, and the quantitation of the basic physiological processes can all be accomplished by the present invention. The testing of patients with the present invention has confirmed generally that it is possible to reduce substantially the dose administered to the patient without any sacrifice of diagnostic accuracy. Alternatively, for given dose amounts, diagnoses can be reached for patients having much lower radioisotope uptakes than may otherwise be tested.

The combined effects of coincident emissions and tomographic modulation provide the synergistic advantages of having a nuclear probe as well as a tomograph. For example, the invention provides the capability of experimentally determining (as a function of time) the absolute radio-emission of selected organs above the background emissions contributed by structures outside the organ of interest. This allows the study of the physiological functions and processes of these organs. Further, the high degree of angular resolution thus obtained allows the organ depth within the body to be determined. Additionally, early measurements, during the flow of the radioactive bolus through the organ, yield clinically useful information on the patient's fractional cardiac output to the organ.

Other objects, features, and advantages of the present invention will become apparent upon consideration of the following detailed description and the accompanying drawings.

BRIEF DESCRIPTION OF THE DRAWINGS

FIGS. 4a-4f illustrates various relative positions of detector units in unfolded ring embodiments of FIG. 3;

FIG. 5 is a block diagram of the electronic architecture for a fixed probe ring embodiment of FIG. 3;

DETAILED DESCRIPTION

Figure 1:
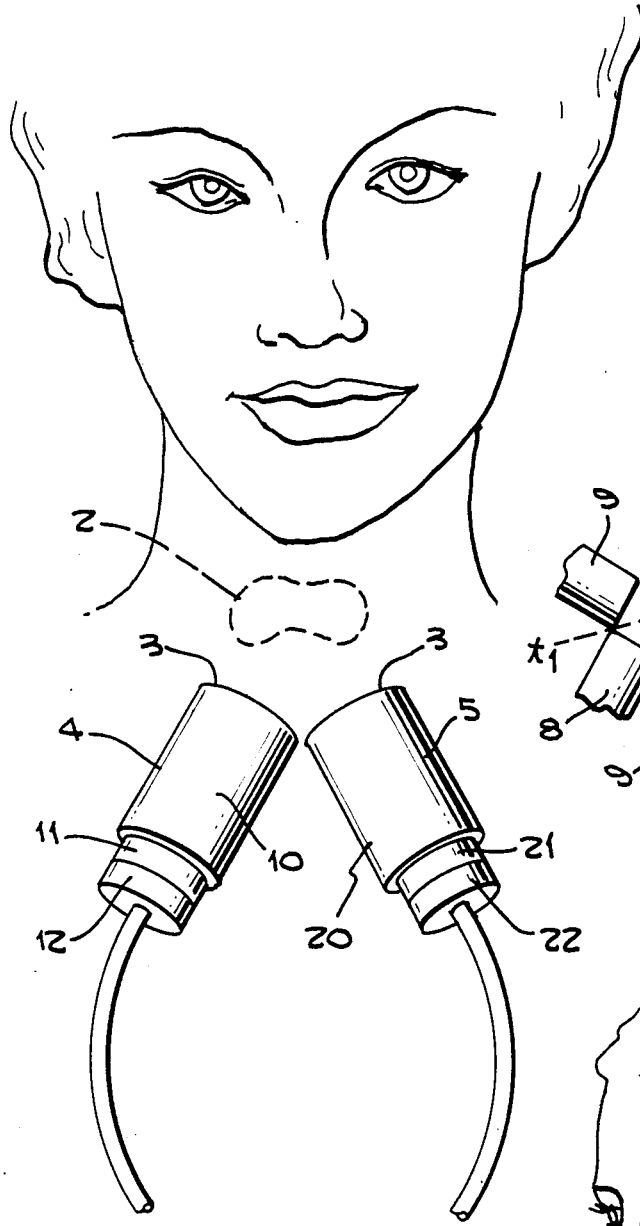
FIG. 1 is a simplified illustration of a rotating probe embodiment of the present invention, shown as used for monitoring emissions from a thyroid into which radiopharmaceuticals have been introduced.
Figure 2:
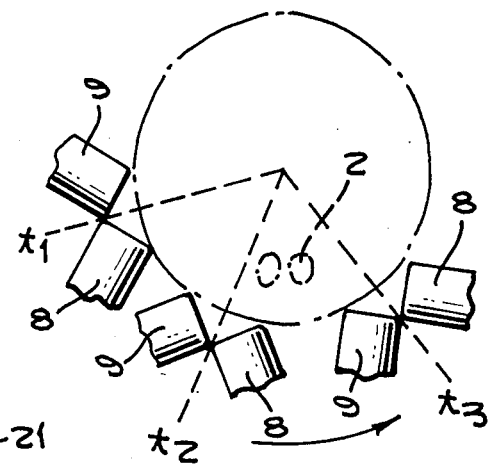
FIG. 2 is an illustration of a cross section of a neck, indicating the positions of the probe as shown in FIG. 1 relative to the thyroid gland at arbitrary times during patient testing.

Referring to FIG. 1, after intravenous injection or oral administration of a suitable radiopharmaceutical into an organ 2 of interest, such as the thyroid gland, the organ becomes itself a source of radioactivity, emitting decay products. For example, for the isotope I-123 of iodine, these products consist of gamma-photons emitted with an energy of 159 keV (kilo electron volts) and x-photons at 28 keV energy. Apart from their different energy values these two types of photons act identically in other relevant respects. Each photon of a given type is emitted with a probability that is characteristic of the photon energy; this probability of emission is the same in all spacial directions. Another isotope of interest, for example, is indium-111, which will emit photons at 173 keV and 246 keV energy levels.

The detector crystals 3 receive all energies of the decay products but their response can be limited to a narrow range. In the probe embodiment of FIG. 1, a single pair of detectors 4, 5 is needed, one tuned to the gamma-photon energy level and the other to the x-photon energy level. Such detectors are commercially available, e.g. conventional sodium crystal detectors, such as those which are manufactured by Oak Ridge Technical Enertprises Corporation (ORTEC), or conventional solid-state detectors constructed of silicon or germanium. Generally, while gamma-photons and x-photons will hit the corresponding detectors at different times, a small fraction of them may be detected simultaneously (i.e., coincident striking photons registering the sum of the energies, in the case of I-123 this would be 187 keV). The detector pair 4,5 makes a sequence of measurements while rotating in a transverse plane perpendicular to the patient's head-to-toe axis. The sense of rotation, that is, the sequence of measurements, (clockwise or anti-clockwise) is irrelevant.

Figure 3:
FIG. 3 illustrates the relative position of a fixed probe ring embodiment of the invention.
Figure 4:
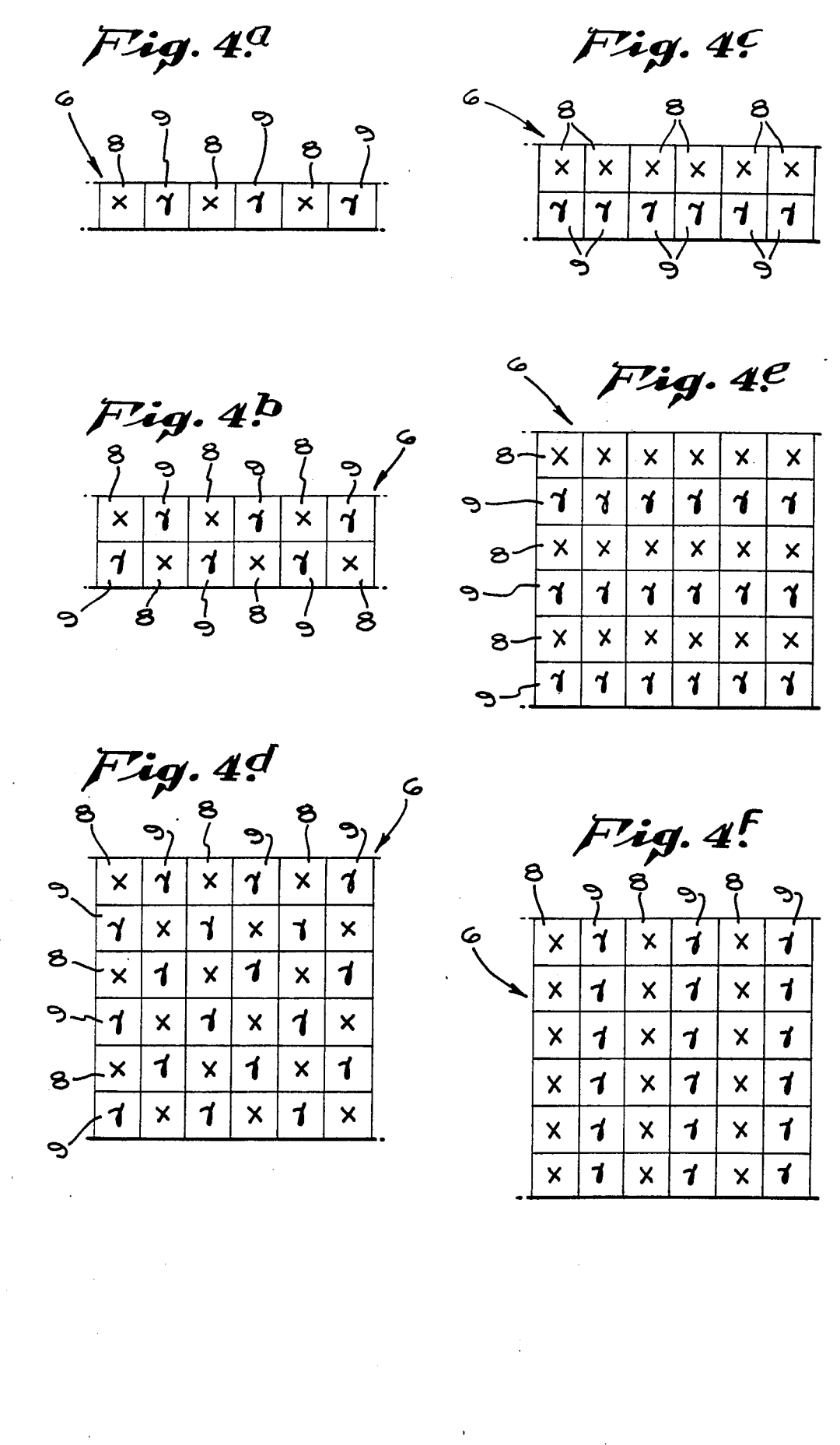

In the preferred arrangement, the detector crystals 3 form a ring embodiment, shown generally at 6 in FIGS. 3 and 4. FIG. 4a shows a portion of a detecting assembly consisting of a single ring 6 of paired detectors 8, 9. The ring 6 has been schematically unfolded in order to show the alternating x-photon detector crystals 8 (28 keV) and gamma-photon detector crystals 9 (159 keV). FIGS. 4b and 4c show a double ring 6 arrangement in a checkerboard pattern and a strip pattern, respectively. FIGS. 4d, 4e and 4f likewise show multiple ring array in either of the two patterns; the strip pattern, in particular, can be horizontally (e) or vertically (f) directed. Any other pattern in which x and gamma detectors are paired to view the same organ region can be used. In each case it is understood that the pattern is extended to form a complete ring.

The electronic circuitry architecture is schematically shown in FIG. 5 for the case of the single ring detector array of FIG. 4a. A conventional high-voltage power supply 1 energizes each of the detector photomultiplier tube assemblies 10, 20, 30, 40, 50, 60. The electrical output signals of assemblies 10, 20, 30, 40, 50, 60 are then fed in succession into the pre-amplifiers 11, 21, 31, 41, 51, 61, the amplifiers 12, 22, 32, 42, 52, 62, the single channel analyzers 13, 23, 33, 43, 53, 63, and the scalers 14, 24, 34, 44, 54, 64, respectively. The single channel analyzers 13, 23, 33, 43, 53, 63 will provide an output pulse from the input received from respective amplifiers 12, 22, 32, 42, 52, 62 only for those pulses from the amplifiers that fall within a selected voltage amplitude range. Hence, the detectors are effectively "tuned" to the detection of either x or gamma photons. The scalers 14, 24, 34, 44, 54, 64 count the output pulses generated by the said analyzers 13, 23, 33, 43, 53, 63, respectively.

The overlap coincidences between the x-photons and gamma photons are recorded by units 13/23, 33/34, 53/63 and the mutual overlap coincidences are recorded by units 23/33, 43/53. The coincidence units are in turn connected to the scalers 15, 25, 35, 45, 55.

A coincidence counter is a device which counts—provides an output pulse—when it receives the sum of two coincidence photon energies received simultaneously. An overlap coincidence counter, therefore, is a coincidence counter which utilizes the output of an x-photon counter and the adjacent gamma-photon counter (and its related circuitry) in the detector array to trigger a third counter to detect the occurence of x-photon and gamma photon coincidence. A mutual overlap coincidence counter is an overlap coincidence counter utilizing the output of one of the pair of detectors in the array with the output of the following counter for the next detector of the next pair in the detector array.

An electronic timer 7 is gated to the several individual scalers 14, 24, 34, 44, 54, 64 and to the coincidence scalers 15, 25, 35, 45, 55. The times during which counts of x, gamma, and coincidence photons are accumulated can thus be pre-programmed prior to patient testing in order to follow any required physiological schedule.

A computer 70 may be coupled to receive signals both from each single channel analyzer 13, 23, etc, and also from the overlap coincidence circuits 13/23, 23/33 etc. over the multiple conductor buses as indicated in FIG. 5. The computer unit 70 may include associated display and graphics circuits to provide graphs similar to both the angular and the radiation vs. time plots as shown in other figures of the drawings. In this regard, it may be appreciated that the ring type sets of detectors as shown at 6 in FIGS. 3 and 4 will provide angular radiation count information appropriate for the plotting of graphs such as those shown in FIGS. 7a through 7d, when the signals from each of the single channel analyzers 13, 23, etc. are coupled separately to the computer 70.

Figure 6:
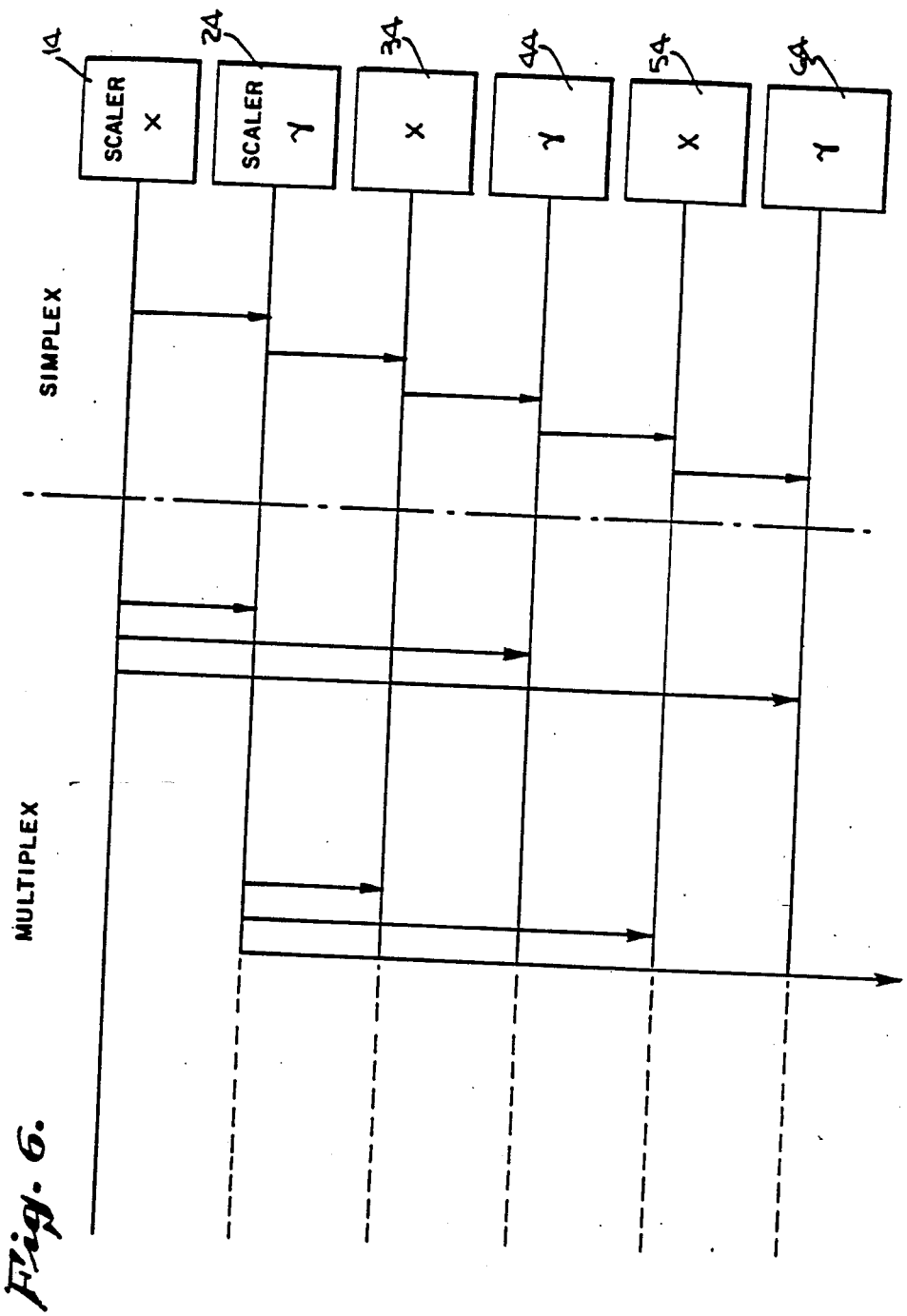
FIG. 6 is a block diagram of a coupling scheme for different variations of the electronic architecture of FIG. 5.

In the arrangement at 12, 22, 32, 42, 52, 62 of FIG. 5, the x and gamma detector crystals are sequentially interconnected as shown in FIG. 6 in simplex circuits 14 and 24, 24 and 34, 34 and 44, 44 and 54, 54 and 64 to provide the coincidence counts registered in the various overlap coincidence units. In order to enhance the number of coincidence counts, which are usually low for small injected doses of radioactivity or for patients with very low uptakes, the multiplex connections of FIG. 6 between any x-detector and all gamma-detectors, and likewise between any gamma-detector and all x-detectors, can be employed.

The components chosen to build the circuitry can be conventional electronic devices. For example, the following devices manufactured by ORTEC may be employed: single channel analyzer model no. 455 (for x-radiation), model no. 551 (for gamma radiation); scaler model no. 431; timer model no. 531; coincidence counter model no. 414; overlap coincidence counter model nos. 778 and 779. The electronic architecture for double or rectangular arrays is based on the same principles as hereinabove described. Additionally, the cross-connections between the individual rings likewise would follow the same principles as those illustrated.

Figure 7B:
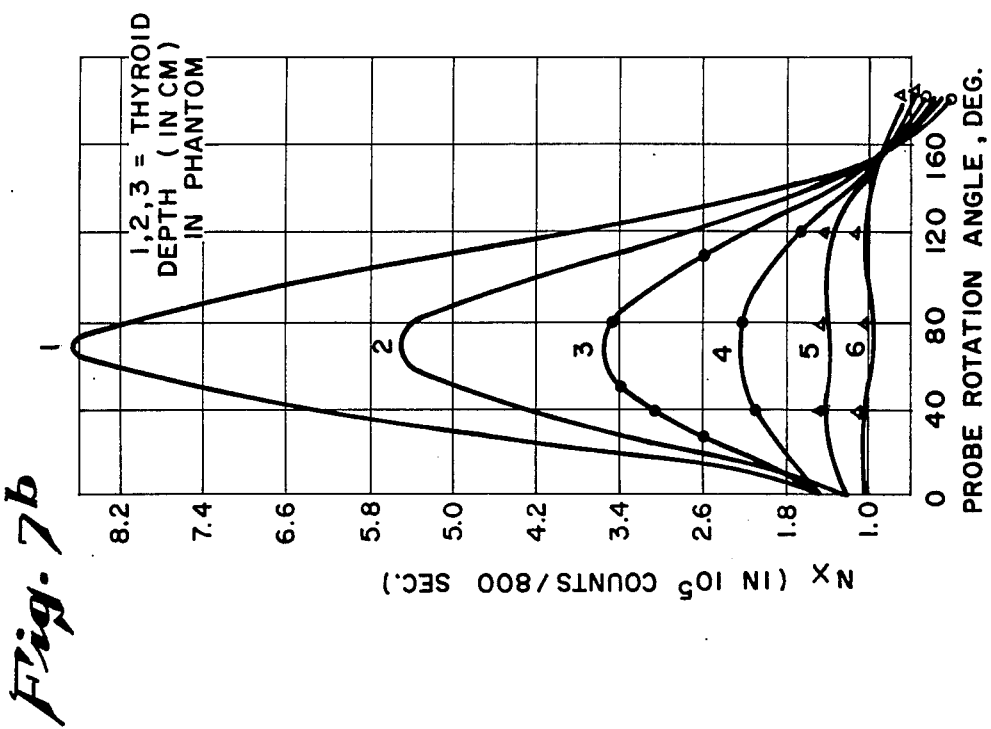
FIGS. 7a–7d are graphical representations of typical output of measurements of gamma, x, and coincidence photon emissions from a healthy gland using the invention as shown in FIG. 1, with the resulting gland radioactivity also being graphed.
Figure 7A:
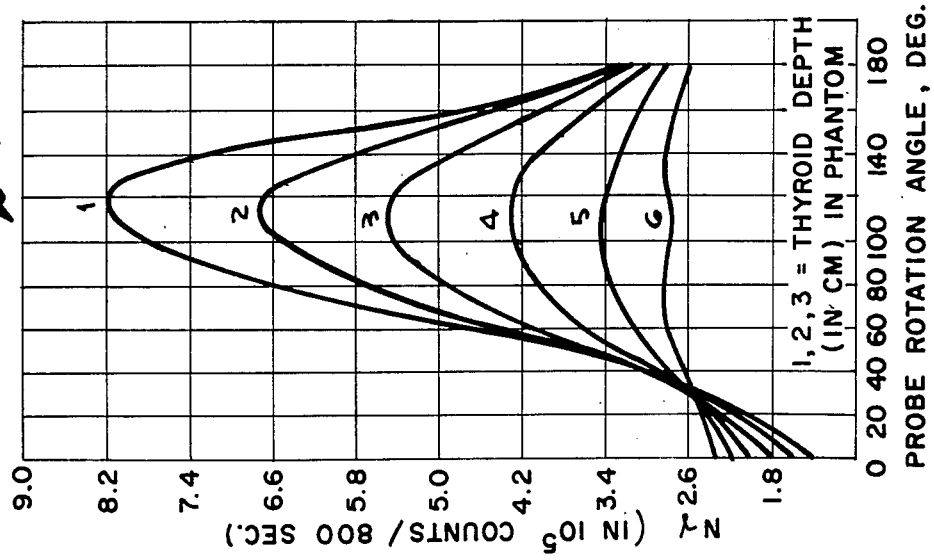
Figure 7D:
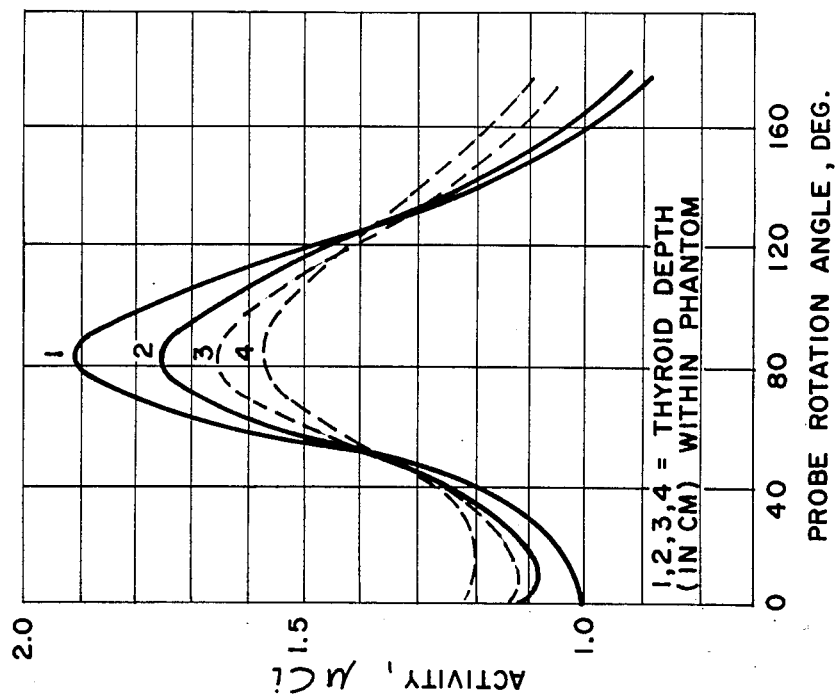
Figure 7C:
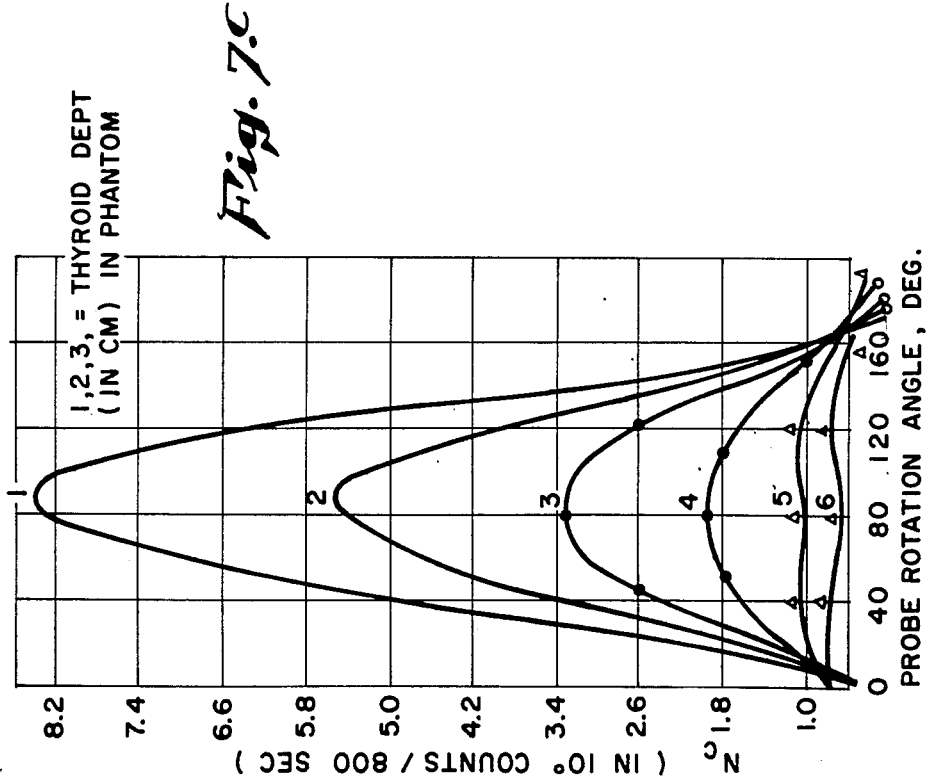

Typical laboratory results obtained with a thyroid phantom (an irradiated lucite disc representing a normal thyroid) are reproduced in FIGS. 7a, 7b and 7c. The photon counts (x, gamma, coincidence) registered over any desired time period (in this example 800 seconds) are graphed therein as a function of probe angle. Emission readings should begin shortly after injection of the radioactive pharmaceutical, typically within the first 10 seconds and preferably within the first 5 seconds. Use of ring configuration 6 is advantageous in that readings can be taken instantaneously. The initial measurements are important in that they describe the physiology of the uptake of the drug by the organ 2.

In the arrangement of FIG. 1, the angle is the value of the rotation angle referred to an arbitrary zero angle position. The counts are corrected so as to take into account the radioactive decay from the start of the test to the time of each individual angular measurement. The several curves correspond to different depths of the thyroid within the neck. The amplitudes of the curves are inversely proportional to the respective depths; thus, the curve labelled (1) corresponds to a location nearest the neck surface (here 1 cm), while curve (6) is for the deepest location (6 cm) considered in the experiment. The two maxima of curve (6) are an accurate manifestation of the two thyroidal lobes. Their period is the same as that introduced by the modulating effect of the probe rotation, that is 360 degrees. The curves are qualitatively similar for all types of photons (gamma, x, coincidence) demonstrating that their shape is dictated principally by the geometric modulation. The different curves exhibit two invariant features: the maxima and minima are respectively angle-synchronous, and they all pass through two nodal points symmetrically located at 90 degrees on either side of these extremal positions.

On the other hand, in the ring arrangement of FIG. 3, a set of curves such as those of FIG. 7 would be obtained in a time-series fashion according to any preset schedule chosen to follow the physiology of the radioactive uptake process rather than by probe rotation. The resulting thyroidal absolute radioactivity has also been graphed in FIG. 7d. the same general features of the modulation have been preserved but the period has now been halved owing to the theoretical expression of activity as a quadratic functional of the number of counts.

Figure 8A:
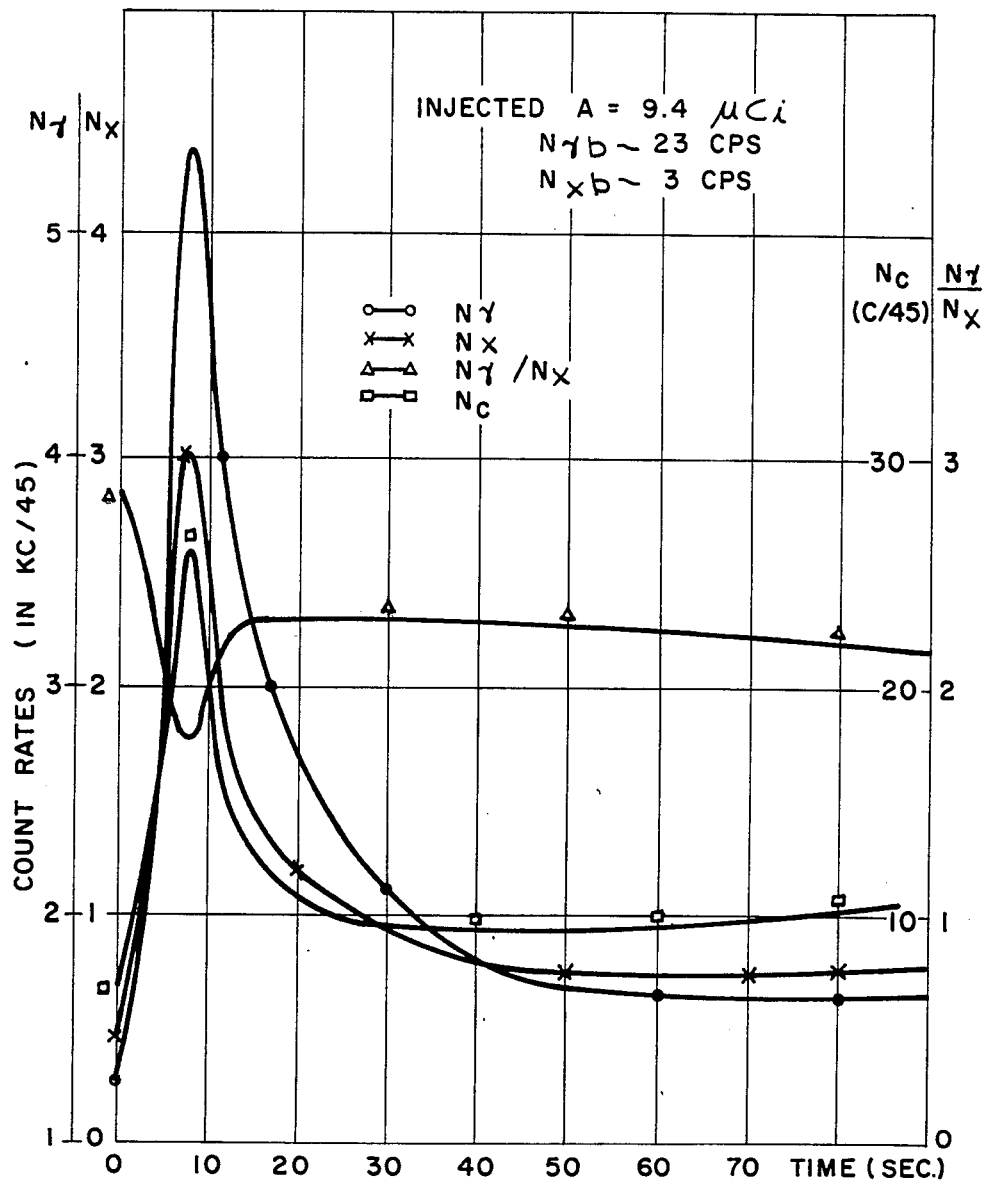
FIG. 8a is a graphic representation of time measurements of the several photon type counts for a patient affected by a disorder of the thyroid gland.

FIG. 8a shows time-measurements of the gamma, x and coincidence counts taken on an actual patient. They depict the time evolution of radioactive uptake in patients afflicted by progressive systemic scleroderma. These curves indicate a lack of accumulation of the radioactive pharmaceutical by the thyroid, i.e. a non-functioning thyroid.

Figure 8B:
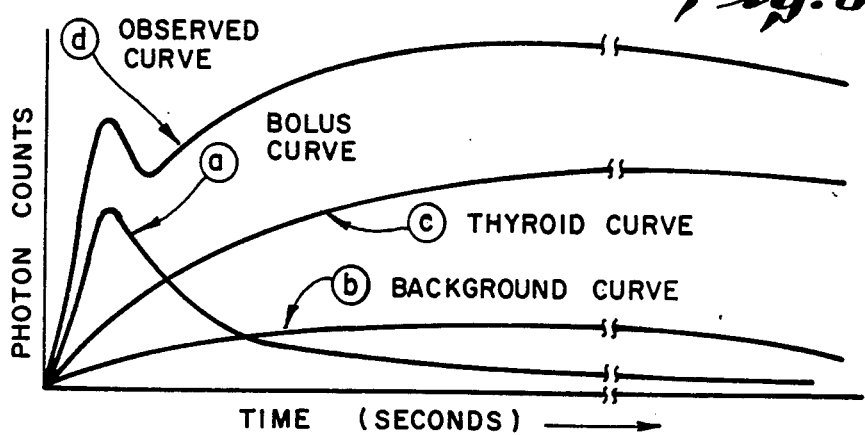
FIG. 8b is a general graphic representation of time measurement configuration of any of the photon type counts for a subject with a healthy thyroid.

In FIG. 8b, the general curves exhibit particular features which are of clinical significance. They represent the end manifestation of three concurrent physico-biological precesses. Curve (a) corresponds to the flow of the radioactive bolus through the thyroid. Its characteristic parameters (such as shape, height of the maximum, ascending and descending slopes, width) are relatable to the physiology of the heart and circulation. The curve can be mathematically described by a distribution function; typically, a modified gamma distribution whose moments are representations of the cardiac output properties. Curve (b) is the cumulative background radioactivity in the neck tissue between the thyroid and the detector crystal. Likewise, curve (c) is the cumulative curve for the thyroid proper. The features of this last curve are descriptive of the gland physiological processes. Thus, the absence of this curve is indicative of a totally non-functioning gland, or an ablated or surgically removed gland. Its ascending part is the result of the progressive cumulation of radioactivity after several passes of the blood flow through the thyroid (that is, the uptake process). The plateau of the curve is the equilibrium regime reached when uptake and discharge of radioactive iodide exactly compensate each other. Much later, the descending slope of the curve describes the imbalance in favor of the loss of radioactive iodide. While both processes occur concurrently, experimental results indicate that trapping dominates in the earlier times while the converse progressively sets in at the later times. The departure of curve (c) from the background curve (b) is a faithful representation of the organ physiology. The steepness of the ascending and descending portions of the resulting curve, and the height of the plateau, are respective measures of the competing trapping and organification processes and of the equilibrium regime. As mentioned above, the background radiation levels as shown in curve (b) of FIG. 8b may be determined by the radiation levels at the nodal points where the plots of FIG. 7 cross.

Hence, a comparison of the curves of FIG. 8a to the observed curve (d) of FIG. 8b clearly shows the difference between a non-functional and healthy thyroid emission, respectively. Thus, in the observed curve "d" of FIG. 8b, the radiation levels observed at the thyroid have a peak, then a minimum, and then remain at a relatively high level, indicating the retention of iodine in the thyroid. In FIG. 8a, however, where the thyroid was nonfunctioning, and there was virtually no retention of the radioactive iodine in the thyroid, the double peak with an intermediate minimum was not present, and the detected radiation near the thyroid soon dropped off to a low level. Incidentally, for a non-functioning thyroid as graphed in FIG. 8a, there would be no point in taking angular measurements, to determine background radiation levels.

Figure 9:
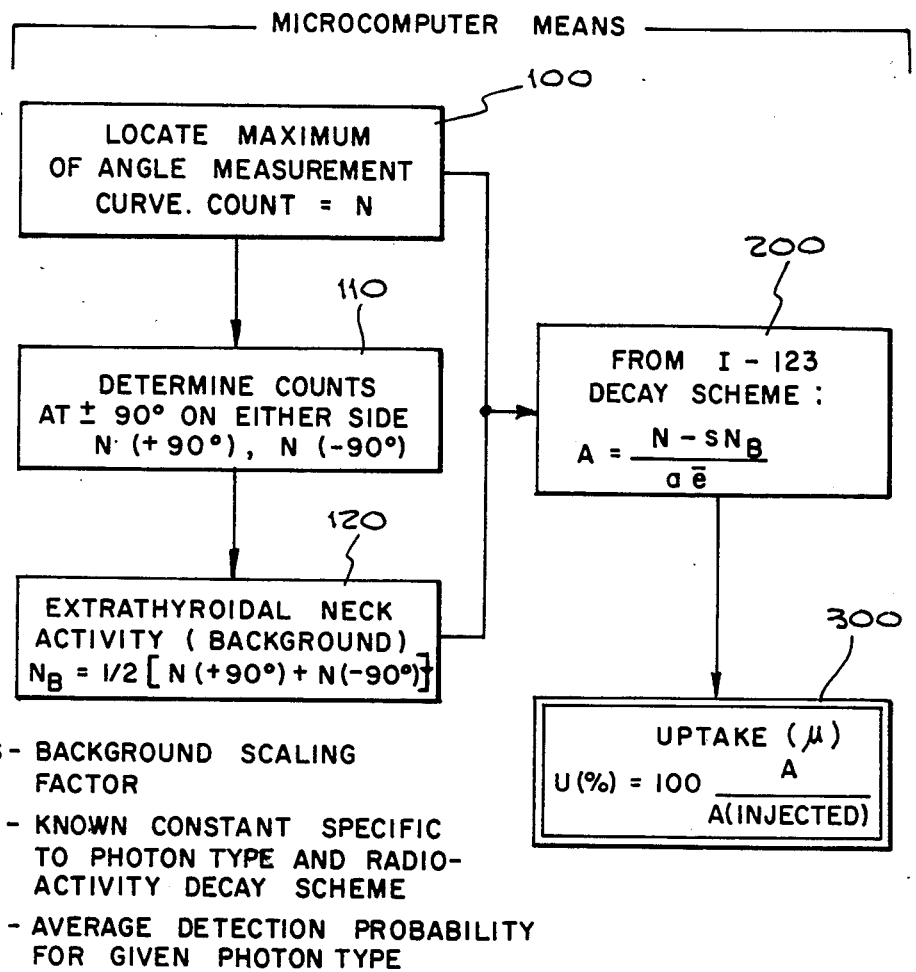
FIG. 9 summarizes the steps involved in determining the thyroidal radioiodine uptake from the measured counts.

FIG. 9 is a block diagram synopsis of the methodology followed to determine the thyroid absolute radioactivity and uptake at any time during the test. These mathematical steps can be readily implemented on a dedicated microcomputer 70. In step 100, the different detectors are interrogated in order to determine the one registering the maximum number of counts. The extra-thyroidal (background) neck activity is provided by the detectors located at 90 degrees on either side of this maximum (110). The average of these two counts (120) will be retained for the background value in order to minimize neck asymmetries. The thyroid absolute activity is obtained in step (200) and the uptake in step (300).

Figure 10:
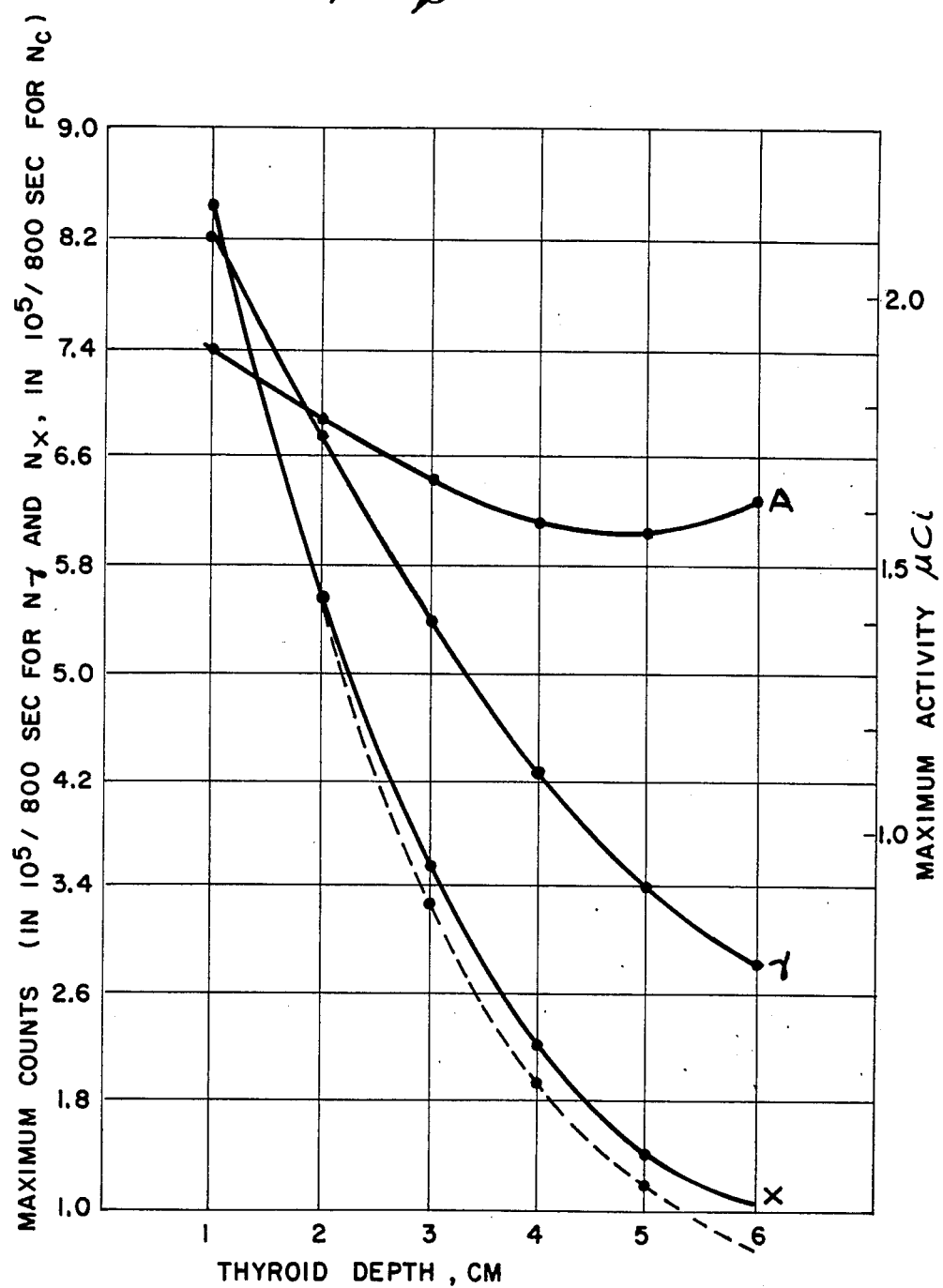
FIG. 10 describes the relationship between the maximum number of counts and the depth of the gland within the neck corresponding to the measurements of FIG. 7.

FIG. 10 illustrates graphically the relationship between the organ depth and the number of counts at step (100) of FIG. 9. This determination assumes that the neck tissue inhomogeneities are so integrated by the detector that the background contribution at the angle of the curve maximum can be inferred from the average of the backgrounds at the nodal points on either side of this position. In this inference, proper scaling is introduced to account for the length difference between the two paths. Then, subtracting the above (scaled) result from the measurement at the angle of the maximum yields the thyroidal contribution emerging from the neck after attenuation in the intervening tissue between the neck surface and the thyroid. With the knowledge of the average tissue attenuation coefficient, straightforward application of the classical attenuation law (Beer - Lambert - Bouguer Law) provides the required gland depth.

In the foregoing description of the present invention, the preferred embodiments have been disclosed. It is to be understood that other variations are within the scope of the present invention.

What is claimed is:

1. A nuclear medicine apparatus for analyzing particular characteristics of a body organ into which radiopharmaceuticals have been introduced, said radiopharmaceuticals causing a plurality of internally generated radioactive emissions from said organ, said apparatus comprising:
   a plurality of pairs of adjacent radiation detector means, each pair of detector means being capable of detecting at least two different internally generated radioactive emissions, of respectively different energy levels, from said organ and generating a plurality of separate electrical signals, each of said separate signals generated in response to a different detected emission; and
   electronic means coupled to said detector means, said electronic means responsive to coincident reception of said two separate electrical signals, representative of said different detected emissions;
   means for processing and analyzing the levels of the coincident reception, coupled to the output of said electronic means, said processing and analyzing means positioned at least every 45 degrees around, the organ being monitored throughout along an arc of at least 180 degrees;
   whereby the maximum and minimum intensity of angular radiation may be determined.

2. The apparatus as set forth in claim 1, wherein each said detector means pair comprises:
   first crystal means, for scintillating visible wavelength radiation, adapted to respond to bombardment by a radioactive emission of higher energy emitted by said organ and generating an electrical signal in response thereto; and
   second crystal means, for scintillating visible wavelength, adapted to respond to bombardment by a radioactive emission of lower energy emitted by said organ and generating an electrical signal in response thereto, wherein said first and second crystal means are adjacent to one-another.

3. The apparatus as set forth in claim 1, further comprising:
   a plurality of preamplifier means for amplifying each said signal, each of said preamplifier means being separately coupled to a respective one of said plurality of pairs of detector means;
   a plurality of amplifier means for further amplifying each said signal, each of said amplifier means being separately coupled to a respective one of said plurality of preamplifier means.

4. The apparatus of claim 1, wherein said electronic means comprises:
   a plurality of single channel analyzer means for conducting only predetermined electrical signals, from among said separately generated signals and within a predetermined voltage range, each of said analyzer means separately coupled to a respective one of a plurality of amplifier means; and
   a plurality of first scaler means for counting said predetermined signals for a predetermined period, each of said first scaler means begin separately coupled to a respective one of said plurality of anlayzer means;
   coincidence counter means for only recording contemporaneous detection of a plurality of said at least two different emissions, each emission represented by said separately generated signal, each one of said counter means being coupled to each one of said plurality of said single channel analyzer means and said first scaler means;
   second scaler means for recording when said separately generated are contemporaneously detected, said second scaler means being separately coupled to a respective one of said coincidence counter means;
   time-gating means for setting the period in which each of said first scaler means accumulates said signals, and for setting the period in which said second scalar means accumulates said separately generated signals when said signals are contemporaneously detected, said time-gating means coupled to each of said first scaler means and said second scalar means; and
   said means for processing and analyzing the levels of coincident reception including digital computer means coupled to said coincidence counter means for monitoring and analyzing the maximum and minimum of said separately generated signals, which are contemporaneously detected at least every 45 degrees through at least an arc of 180 degrees around said organ, such that measurements of absolute radioactivity and an absolute background radioactivity are concurrently determined.

5. A nuclear medicine apparatus for monitoring and analyzing the morphology and physiology of a body organ into which radiopharmaceuticals have been introduced, comprising:
   a plurality of pairs of abutting, single energy, radiation detector means for detecting at discrete angles a relatively high energy, internal, radioactive emission and a relatively low energy, internal, radioactive emission, respectively, from said organ and generating a separate electrical signal in response to each said detected emission respectively;
   each of said pairs of detector means being located at respectively different positions around the perimeter of said organ, said pairs of detectors being located not more than 45 degress apart through an arc of at least 180 degrees around the perimeter of said organ;
   a plurality of amplifying means, for amplifying said electrical signal from said respective detector means, each of said amplifying means being separately coupled to a respective one of said plurality of detector means;

a plurality of discriminator means for suppressing only predetermined electrical signals outside a predetermined voltage range, each of said discriminator means being separately coupled to a respective one of said plurality of amplifying means and for providing an output signal upon the receipt of said predetermined electrical signals as the input within a predetermined voltage range;

a plurality of first counting means for recording said signals from said discriminator means for a predetermined period, each of said first counting means being separately coupled to a respective one of said plurality of discriminator means;

a plurality of coincidence counter means for determining only the simultaneous detection of said high energy emission and said low energy emission, represented by said electrical signals, respectively, each of said coincidence counter means being separately coupled to at least two of said discriminator means so that each of said pairs of detector means are interconnected and their coincidently received radiations are counted, and that adjacent high and low radiation detector means in different pairs are interconnected and their coincidently received radiations are counted;

pre-programmable timer means coupled to each one of said plurality of first counting means and to each one of said plurality of coincidence counter means, for setting the period in which said plurality of first counting means accumulates said emissions, represented by said signals, and for setting the period in which said plurality of coincidental counter means accumulates said simultaneously detected emissions; and computer means, operatively associated with said coincidence counter means, said first counting means, said timer means, and said discriminator means, for monitoring and analyzing the maximum and minimum number of coincidental detection counts over a preset interval of said low energy emissions and said high energy emissions at no more than 45 degrees apart through an arc of at least 180 degrees around said organ such that absolute radioactivity and absolute background radioactivity is concurrently determined, whereby detected emissions and a counted coincidence of said emissions of said photons are indicative of both the morphological and physiological features of said organ.

6. An apparatus as set forth in claim 5, wherein said plurality of pairs of detector means are contiguously arranged in a ring around the organ.

7. An apparatus as set forth in claim 5, wherein each of said plurality of pairs of detector means comprises:
an x-radiation detector means, for registering x-ray photons emitted by said organ and generating and electrical signal in response thereto; and
a gamma-radiation detector means, for registering gamma-rays emitted by said organ and generating an electrical signal in response thereto.

8. An apparatus as set forth in claim 7 further comprising:
said plurality of pairs of detector means forming a plurality of collars, said detectors means mounted axially and contiguously superposed to form a two-dimensional array of vertically alternating x-radiation and gamma-radiation detectors.

9. An apparatus as set forth in claim 7 further comprising:
said plurality of pairs of detector means forming a plurality of collars axially and contiguously superposed to form a two-dimensional array of both vertically and horizontally alternating x-radiation and gamma-radiation detectors.

10. An apparatus as set forth in claim 5, wherein said plurality of pairs of detector means are arranged to form a collar, each of the pairs of detector means being mounted superposed axially and contiguously relative to each other.

11. An apparatus as set forth in claim 10, wherein:
each of said pairs of detector means are alternatively comprised of a plurality of x-radiation detectors and a plurality of gamma-radiation detectors.

12. A method for concurrently monitoring and analyzing the morphology and physiology of a body organ following introduction of a radiopharmaceutical comprising the steps of:
measuring photons of two different energy levels characteristic of the radiation output from said radiopharmaceutical for a predetermined period of time and at discrete angles around the organ, including angles spaced apart by not more than 45 degrees, through at least 180 degrees;
determining the angular distribution of the output radiation containing both of said two different energy levels around that portion of the human body where the organ is located; and
comparing the determined angular radiation distribution with that expected for a normal healthy organ, for diagnostic purposes.

13. The method as set forth in claim 12, wherein the radiation distribution is further determined by:
concurrently deriving the absolute radioactive background emission and radioactivity of tissues extraneous to the organ undergoing testing by deriving an average from the absolute radioactive outputs at characteristic angles.

14. The method as set forth in claim 12, wherein the radiation distribution is further determined by:
concurrently determining the absolute activity and radiopharmaceutical uptake of selected organs from measuring the radiation output for a predetermined period of time.

15. The method as set forth in claim 12, wherein the radiation distribution is further determined by:
the physiologic functions of uptake and retention of radiopharmaceuticals by said organ measuring the radiation output for a predetermined period of time.

16. A method for concurrently monitoring and analyzing the morphology and physiology of a body organ following bolus introduction of a radiopharmaceutical, comprising:
measuring photons of two different energy levels characteristic of the radiation output from said radiopharmaceutical for a predetermined period of time and at discrete angles around the organ;
determining the angular distribution of the output radiation containing both of said two different energy levels around that portion of the human body where the organ is located, including angles spaced apart by not more than 45 degrees through at least 180 degrees;

determining the angle of maximum absolute coincident radiation emission;

concurrently determining the overall absolute background radiation and absolute radioactivity of tissues extraneous to the organ undergoing testing from the average of absolute radioactive emissions detected at an angle approximately plus 90 degrees and at an angle approximately minus 90 degrees from said maximum angle;

concurrently determining the absolute radioactivity from said organ;

concurrently determining the flow of the radioactive bolus throught the said organ;

subtracting the absolute background radiation from the absolute radioactivity to determine the absolute uptake radioactivity of said organ;

concurrently plotting the total absolute radiation with time detected from the organ, the absolute background radiation with time, the absolute uptake radioactivity with time, and the flow of the radioactive bolus with time;

whereby the a clinical evaluation of the morphology and physiology of said organ can be rendered.

17. A method for concurrently monitoring and analyzing the morphology and physiology of a body organ following introduction of a radiopharmaceutical, comprising:

measuring photons of two different energy levels characteristic of the radiation output from said radiopharmaceutical at discrete angles around the organ;

determining the angular distribution of the output radiation containing both of said two different energy levels around that portion of the human body where the organ is located, including angles spaced apart by not more than 45 degrees through at least 180 degrees;

determining the angle of maximum absolute coincident radiation emission;

concurrently determining the overall absolute background radiation and absolute radioactivity of tissues extraneous to the organ undergoing testing by comparing the measurement of absolute radioactive emissions detected at an angle approximately plus 90 degrees with the measurement of emissions at an angle approximately minus 90 degrees from said maximum angle and deriving an average value for absolute radioactive emissions;

concurrently determining the absolute radioactivity from said organ; and substracting the absolute background radiation from the absolute radioactivity to determine the absolute uptake radioactivity of said organ;

whereby a clinical evaluation of said organ can be rendered.

* * * * *